United States Patent [19]
Ramwell

[11] 3,993,057
[45] Nov. 23, 1976

[54] INTRAUTERINE DEVICE THAT BIOERODES IN RESPONSE TO THE ENVIRONMENT OF THE UTERUS AND METHOD OF USING

[75] Inventor: Peter W. Ramwell, McLean, Va.

[73] Assignee: Alza Corporation, Palo Alto, Calif.

[22] Filed: May 19, 1975

[21] Appl. No.: 578,727

Related U.S. Application Data

[62] Division of Ser. No. 318,890, Dec. 27, 1972, Pat. No. 3,888,975.

[52] U.S. Cl. .................................. 128/130; 128/260
[51] Int. Cl.² ............................................ A61F 5/46
[58] Field of Search ............. 128/130, 260; 424/15, 424/22

[56] References Cited
UNITED STATES PATENTS

| | | | |
|---|---|---|---|
| 3,803,308 | 4/1974 | Zipper | 128/260 X |
| 3,845,761 | 11/1974 | Zaffaroni | 128/260 |
| 3,880,991 | 4/1975 | Yolles | 424/22 |
| 3,896,819 | 7/1975 | Zaffaroni | 128/130 |
| 3,903,880 | 9/1975 | Higuchi et al. | 128/130 |

*Primary Examiner*—Lawrence W. Trapp
*Attorney, Agent, or Firm*—Paul L. Sabatine; Edward L. Mandell; Thomas E. Ciotti

[57] ABSTRACT

An intrauterine device for administering drug locally to the uterus at a controlled rate for a prolonged period of time is disclosed. The device contains a body of polymer capable of bioeroding in the environment of the uterus over a prolonged period of time. This body has the drug dispersed throughout so that as the body gradually bioerodes, it slowly releases the dispersed drug. In a preferred embodiment, the device releases a uterine contraction-inducing prostaglandin locally to the uterus at a controlled rate over a prolonged period of time.

47 Claims, 7 Drawing Figures

INTRAUTERINE DEVICE THAT BIOERODES IN RESPONSE TO THE ENVIRONMENT OF THE UTERUS AND METHOD OF USING

Cross Reference To Related Application

This application is a division of U.S. application Ser. No. 318,890 filed on Dec. 27, 1972, and now U.S. Pat. No. 3,888,975, with both applications assigned to the same assignee.

BACKGROUND OF THE INVENTION

Field of the Invention

This invention relates to a bioerodible intrauterine device for delivering drugs to the uterus at a controlled, continuous rate over a prolonged period of time. In preferred embodiments it concerns a bioerodible intrauterine device which enables the improved administration of pregnancy-interrupting drugs.

The Prior Art

Presently, a critical need exists for an acceptable means for the direct continuous delivery of drugs directly to the uterus for gynecological, endocrinological and reproductive physiological purposes.

In the prior art, it is most common to administer such drugs systemically, such as by injection, by ingestion or by intravenous infusion. Often, with systemic administration, the amount of drugs needed to achieve the desired gynecological, endocrinological or reproductive physiological purpose is so large that serious undesirable side effects occur, ranging from migraine headaches, vomiting, fatigue and nausea, to jaundice and pulmonary embolism. It has been found in many cases that direct local application of these agents to the uterus in smaller than systemic dosages can bring about the desired effects with much reduced side effects. For example, Wiqvist and Bygleman (*Lancet*, 1970, ii, page 716) showed that prostaglandins, drugs useful for reproductive physiological purposes, are 10 times more active as agents for causing uterine contractions when administered locally to the uterus than when administered intravenously. Side effects were reduced as well. Miller, Calder and MacNaughton (*Lancet*, July 1, 1972, page 5) showed that dosages of drugs for certain purposes can be reduced even further by applying them locally to the uterus in a continuous fashion. These investigators required a complicated system of pumps, tubes and catheters to achieve a continuous flow of drugs to the uterus, however. Thus it would not be possible for the patient to be ambulatory. Neither would it be convenient to deliver a continuous flow of drugs to the uterus over a prolonged period, as is often desirable, with such an apparatus.

Vaginal suppositories are a well known drug form which has been used to administer drugs to the uterus, since some of the vaginally administered drug which is absorbed through the vaginal walls passes via the circulatory system to the uterus. This method of delivery is essentially systemic and thus has the same serious side effects.

A device capable of locally releasing drugs to the uterus at a controlled rate over a prolonged period of time which is small enough to be contained within the uterus and simple enough in operation to give reliability and avoid mechanical malfunctions would be of great utility. Such a device would, for example, fill the critical need which now exists for an acceptable method for delivering progestational and estrogenic hormones directly to the uterus, and for delivering uterine contraction-inducing agents directly to the uterus.

OBJECTS OF THE INVENTION

Accordingly, it is an object of the present invention to provide a device for the local delivery of drugs to the uterus.

Another object of the present invention is to provide a device which may be contained within the uterus and/or the cervix uteri and which is capable of delivering drugs locally to the uterus continuously over a prolonged period of time.

Yet another object of the present invention is to provide an intrauterine device which is of simple operation and which reliably delivers drug over a prolonged period of time.

A further object of this invention is to provide an improved method for delivering drugs to the uterus at a controlled, and if desired, constant rate.

Another object of this invention is to provide a drug dispensing uterine insert for delivering drugs to the uterus with increased efficacy.

A still further object of this invention is to provide a drug-releasing intrauterine device which will be of a uterine-retentive configuration during the period of drug release but of a configuration suitable for removal from the uterus following drug delivery.

Yet another object of this invention is to provide a device for locally administering a controlled amount of a uterine contraction-inducing drug to the uterus at a controlled rate which will remain in the uterus or cervix uteri during the term of drug administration.

These and other objects, features and advantages of the present invention will be readily apparent to those versed in the art from the following description of the invention and the accompanying claims.

STATEMENT OF THE INVENTION

In attaining the objects of this invention, a drug delivery device is provided which, in its broadest aspects, comprises a body of a polymer having drug dispersed therethrough, said polymer being capable of bioeroding in the environment of the uterus over a prolonged period of time. The device is of a shape and size adapted for insertion and retention in the uterus and/or cervix uteri. As the body of polymer gradually erodes it releases the dispersed drug at a controlled rate.

In one embodiment, the device is adapted to deliver estrogenic hormones to the uterus over periods of from a few hours to several weeks.

In another embodiment the device incorporates a progestational agent and gradually releases said agent over a prolonged period of time.

In a preferred embodiment this invention involves a device of a shape suitable for insertion and retention in the uterus or cervix uteri of a pregnant female comprising a body of polymer bioerodible in the environment of the uterus which contains a uterine contraction-inducing prostaglandin dispersed therethrough. The prostaglandin is released continuously over a period of several hours as the polymer erodes, and induces uterine contractions during the period of release. This induction of uterine contractions finds application in the area of childbirth and in the area of therapeutic abortion.

BRIEF DESCRIPTION OF THE DRAWINGS

In the drawings wherein like reference numerals designate like parts.

DETAILED DESCRIPTION OF THE INVENTION

In attaining the novel objects, features and advantages of the invention, it has now been surprisingly found that drugs may be most advantageously locally delivered to the uterus over a prolonged period of time by being incorporated in a body of material which slowly bioerodes in the environment of the uterus, said body of material being incorporated in a device adapted for insertion and retention in the uterus or cervix uteri throughout the period of drug administration.

The term "bioerodible", as used in the specification and claims, is defined as the property or characteristic of a body of material to innocuously disintegrate or break down as a unit structure or entity, over a prolonged period of time, in response to the environment in the uterus by one or more physical or chemical degradative processes, for example by enzymatic action, oxidation or reduction, hydrolysis (proteolysis), displacement, e.g., ion exchange, or dissolution by solubilization, emulsion or micelle formation. The products of such bioerosion are thereafter absorbed by the uterus and surrounding tissues, or otherwise dissipated, such as by elimination from the uterine cavity.

As used in the instant specification and appended claims, the term "prolonged period of time" is meant to include time intervals of from at least 3 hours to approximately 30 days or higher and preferably periods of from 4 hours to 48 hours. It should be noted that this term is applied with reference to the time interval over which the drug is released and also with reference to the time interval over which the uterine device and its component materials bioerode in the environment of the uterus, although each of the aforesaid time periods may not necessarily be concurrently coextensive in duration.

With these definitions in mind, and before examining the materials employed in and delivered by the instant devices, let us now turn to the drawings in more detail.

Figure 1:
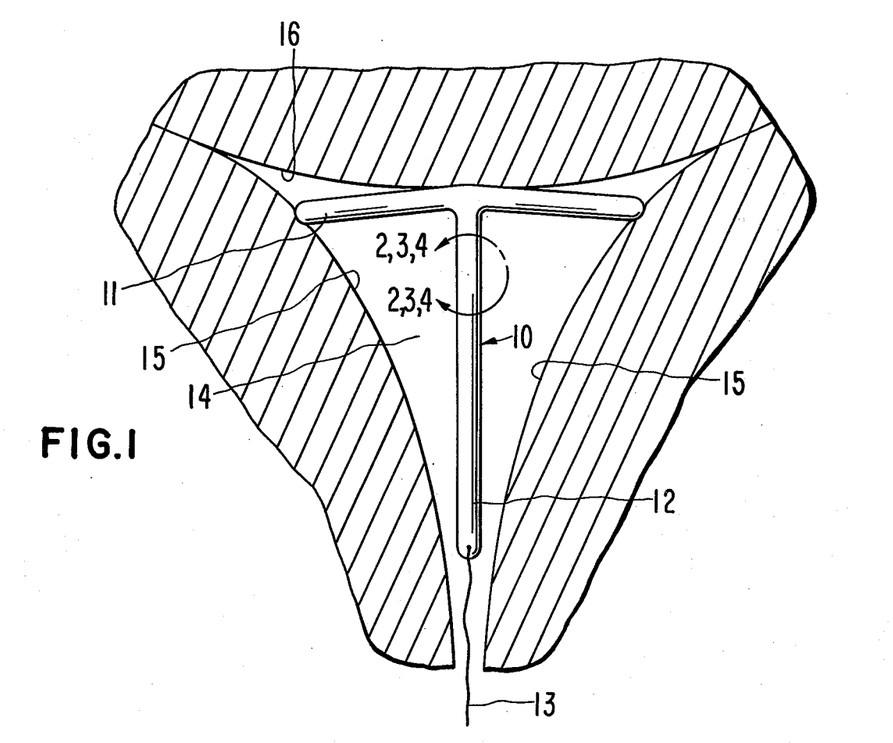
FIG. 1 is an elevational cross-sectional view showing an intrauterine drug delivery device in accord with this invention in place in a uterus.

In FIG. 1 there is depicted an intrauterine drug delivery device in accord with the present invention. This device, drug delivery device 10, is in a shape suitably described as a T. Device 10 is comprised of a cross bar 11 and a depending member or leg 12. Device 10 is of a size and shape adapted to be inserted into the uterus 14 and be retained there over the prolonged period of time for which drug is delivered. The device suitably contacts the sides 15 of the uterus as well as the fundus uteri 16. Device 10 is preferably designed with rounded non-traumatizing ends and a thread 13, attached to the trailing end of leg 12 for manually removing device 10 from uterus 14.

Figure 2:
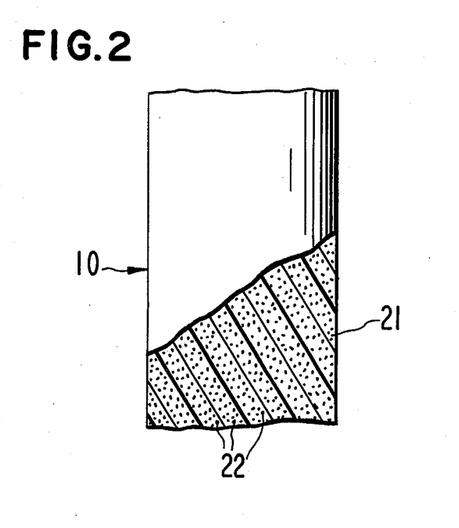
FIGS. 2, 3 and 4 are cut-away views of a section of the device illustrated in FIG. 1 in enlarged scale showing alternate constructions of such a device.

Device 10 is formed of a bioerodible material as will be described and contains drug dispersed therethrough. This construction is shown in FIG. 2, an expanded and cut away view of device 10 at A. As shown in FIG. 2 Device 10 can be a solid body 21 of erodible material which has drug 22 dispersed throughout. As body 21 bioerodes, it releases entrapped drug 22 and delivers it locally to the uterus in which it is positioned. Drug 22 may be in the form of solid particles, liquid droplets, colloidal particles, or gels, depending upon the nature of the drug. When device 10 is of the construction shown in FIG. 2, it releases drug at a controlled rate over a prolonged period of time. As the device erodes, its surface area decreases. This decrease in area causes the rate of drug release to decrease as well. One way to achieve a more constant rate of drug release is to vary the concentration of drug within the body of erodible material 21, increasing the concentration in the inner areas of device 10 so as to compensate for the decrease in area. As an aside, it will be readily appreciated that other variations of drug concentrations throughout the body of erodible material can bring about other patterns of drug release, for example sinusoidal, intermittant and the like.

Figure 3:
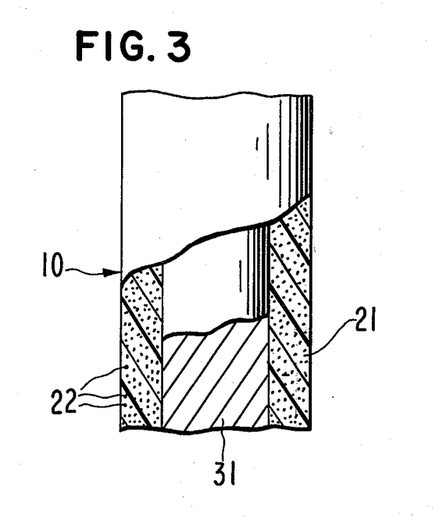

Another way to achieve an essentially uniform rate of drug release, that is, a release having a more nearly zero order time dependence, involves constructing the device as illustrated in FIG. 3. In FIG. 3 erodible material 21 and drug 22 are in the form of an outer layer surrounding an inner core 31. Core 31 is made of a non-erodible material which does not contain drug. It functions as a structural member. It is preferably formed of a flexible material, very suitably a polymer, having an elastic memory. This enables device 10 to be compressed into an easily insertable form for insertion and then to expand in the uterus to a more retentive form. By employing erodible material 21 and drug 22 only as an outer layer, the variation in surface area of drug-containing material is reduced and a more nearly constant rate of drug release is achieved.

Figure 4:
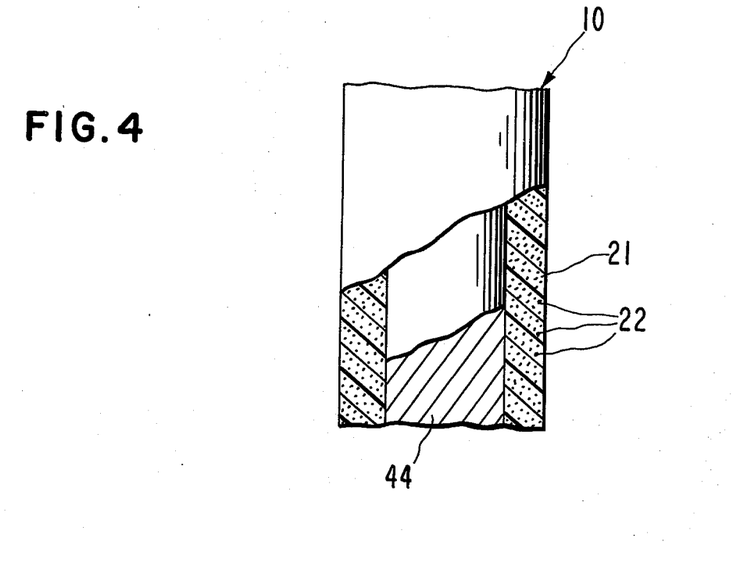

In FIG. 4, yet another alternative construction for device 10 is illustrated. In FIG. 4, an inner core 41 is employed. Core 41 differs from core 31 in that it is formed of an erodible material. This construction offers the advantages of a more constant rate of release, as does the construction shown in FIG. 3 and, also, eliminates the need to remove the device from the uterus at the completion of the drug delivery.

With any of the constructions shown, it would be possible to employ more than one drug either together or in separate layers. For example, in the construction set forth in FIG. 4, one drug could be present and released from material 21 while a second drug could later be released from the erodible inner core.

Figure 5:
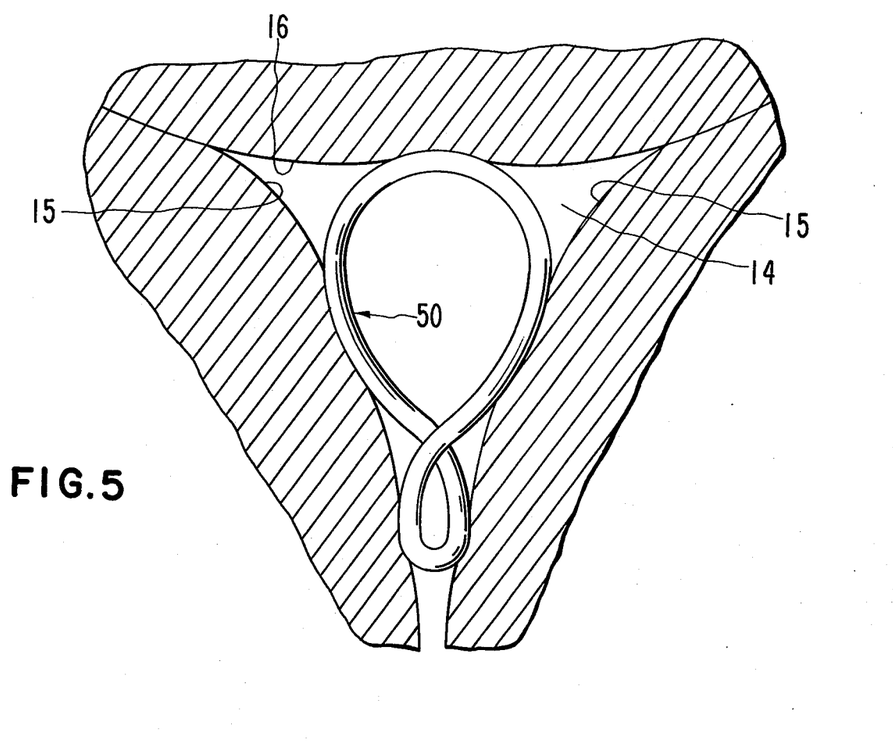
FIG. 5 is an elevational view of another typical configuration for a device in accord with the present invention.

The T-shape of device 10 as illustrated in FIG. 1, while a form which is excellently retained in the uterus, is merely illustrative. FIG. 5 shows another suitable shape for an intrauterine device in accord with the present invention. FIG. 5 illustrates device 50, which is in the shape of a double loop, that when inserted into uterus 14 touches the walls 15 and the fundus uteri 16.

The devices of this invention may take on a great variety of sizes and shapes. For application and retention in the human uterus, they generally range in size from about 2 cm to about 6 cm in length and width. For uterine devices for other animals, larger or smaller sizes may be used as required for comfort and uterine retention. The device may take forms such as cylindrical, bullet, elliptical, circular, bulbous, loop, bow, which lend themselves to intrauterine placement or lodging in the cervix uteri. Specific suitable forms include, without limitation, Birnberg's Bow shown in U.S. Pat. No. 3,319,625, the comet shown in U.S. Pat. No. 3,256,878, the spring of U.S. Pat. No. 3,397,691, Lippes' Loop, the ring with tail, the Ota ring, and the like.

When the device itself is bioerodible it is possible to employ many configurations having excellent uterine retention characteristics which were not of choice previously. A very retentive shape, almost by definition, would be very difficult to remove from the uterus or cervix uteri conventionally, without risk of harm to the delicate tissues in these areas. When the body of the device itself, in addition to its drug release components, is bioerodible, it can break down from a retentive form to an easily removed or expelled form. The entire body may be erodible or only parts, such as joints, may be erodible. Either way, the retentive configuration can be destroyed.

This feature is of especial advantage when delivering drugs which cause uterine contractions, that is, oxytoxic drugs. In such applications, it is desired to have a configuration which will remain in the uterus or cervix uteri throughout the period of drug administration. Such a configuration must be very highly retentive as the contracting uterus is attempting to expel its contents, including the drug delivery device.

Devices capable of remaining in the uterus during uterine contractions would in many cases be most difficult to remove manually. Thus, it is very desirable to fabricate them at least in part from an erodible material.

Drugs which induce uterine contractions are administered to bring about childbirth or to cause therapeutic abortion. In either case the placement of a drug delivery device in the uterus or cervix uteri will have to take into account the presence of the embryo or fetus in the uterus. The device must also be of a design which will permit the contents of the uterus, save the device, to be expelled.

Figure 6:
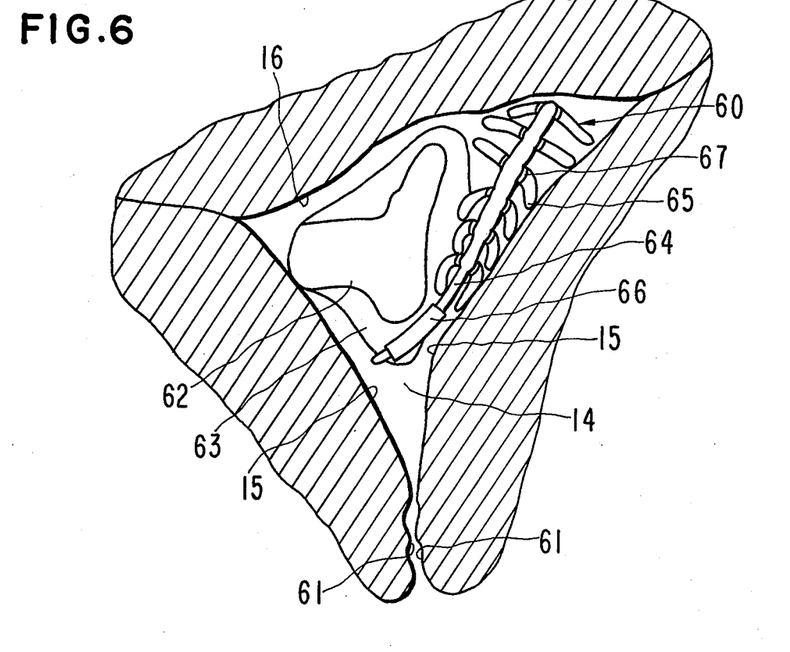
FIG. 6 is an elevational cross-sectional view showing a device of this invention in use in a pregnant uterus.
Figure 7:
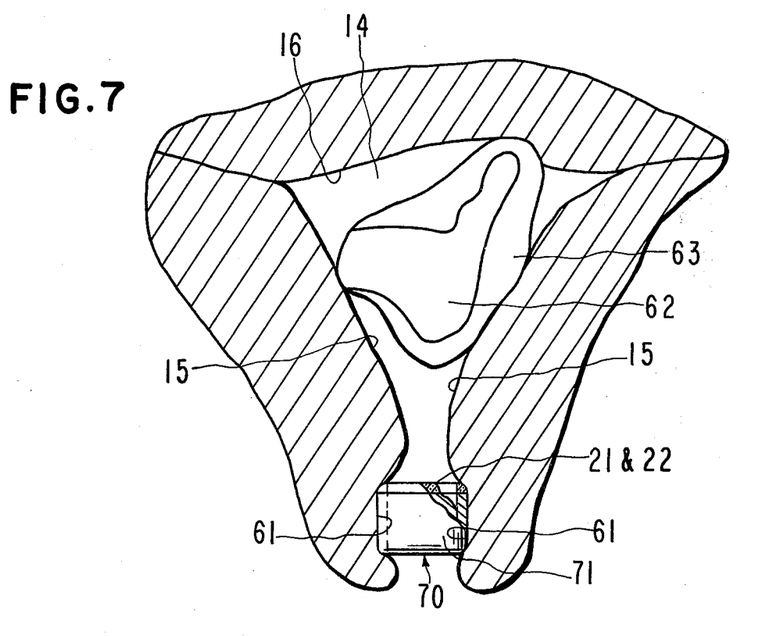
FIG. 7 is a partially sectioned elevational view of a device of this invention adapted for placement in the cervix of a pregnant female.

FIGS. 6 and 7 are enlarged views of two typical devices suitable for administering uterine contraction inducing drugs in use. In FIG. 6 a device 60 in accord with the invention is shown positioned within uterus 14 defined by fundus uteri 16 and walls 15 which walls also define cervix uteri 61. Present in uterus 14 is embryo 62 surrounded by amnion 63 and amnionic fluid. Device 60 is in the form of a multi cross-armed T having a center post 64 and a plurality of cross arms 65. Device 60 is highly flexible and is inserted into the uterus around embryo 62 in an easily insertable collapsed form. Device 60 does not block the path from the uterus 14 through cervix 61. Firmly attached to device 60 is a sleeve 66 of bioerodible material having uterine contraction inducing drug dispersed therethrough. In the uterus the bioerodible material bioerodes and releases its drug causing the uterus to contract and expel embryo 62, amnion 63 and the like. Device 60 remains in the uterus. Cross arms 65 are bonded to center bar 64 via erodible bridges 67. At a point in time after the drug has been released, bridges 67 erode, causing the cross arms 65 to drop off device 60. The resulting separate cross arms and center bar are not retained in the uterus and are easily and harmlessly expelled.

Turning to FIG. 7, the uterus and embryo of FIG. 6 are again shown. A device 70, in the form of a hollow cervical cylinder, is illustrated. Device 70 is shown inserted into the cervix uteri 61. Because of its hollow configuration, it does not block the path through cervix. In fact, it actually serves to dilate the cervix. Device 70, as the cut away shows, is in the form of two axially joined coaxial rings, a top ring of bioerodible polymer 21 containing uterine contraction inducing drug 22 and a bottom ring 71 not containing drug. In use drug 22 is released causing uterus 14 to contract and expel embryo 62 through the center hole of device 70. Bottom ring 71 may be erodible if desired. It may also be of a material swellable in uterine fluids to enhance its retention in the uterus.

It will be appreciated that the device of this invention may take on many other forms, these shown being merely illustrative.

Turning now to the materials employed in these devices, bioerodible materials suitable for fabricating the intrauterine devices are the materials that are non-toxic and non-irritating to the endometrium of the uterus, and which upon bioerosion produce end products that are also nontoxic, non-irritating and safely and easily eliminated from the body.

Exemplary bioerodible materials include both natural and synthetic materials such as (a) structural proteins and hydrocolloids of animal origin; (b) polysaccharides and other hydrocolloids of plant origin; and (c) synthetic polymers. Some of these matrix materials are suitable as in their native form but others, particularly hydrocolloids, require insolubilization either by chemical modification, or physical modification, such as orientation, radiation cross-linking, etc. Exemplary of the first category are: native and modified collagens, muscle proteins, elastin, keratin, resilin, fibrin, etc. Exemplary of polysaccharides and plant hydrocolloids are: aligin, pectin, carrageenin, chitin, heparin, chondroitin sulfate, Agar-agar, Guar, locust bean gum, gum arabic, gum Karaya, tragacanth, gum Ghatti, starch, oxystarch, starch phosphate, carboxymethyl starch, sulfaethyl starch, aminoethyl starch, amido ethyl starch, starch esters such as starch maleate, succinate, benzoate and acetate, and mixtures of starch and gelatin; cellulose and its derivatives such as modified cellulosics, such as partially hydroxyethylated cotton obtained by the treatment of cotton with ethylene oxide or partially carboxymethylated cotton obtained by the treatment of cotton with caustic and choroacetic acid. Exemplary of synthetic polymers are: poly(vinyl alcohol), poly(ethylene oxide), poly(acrylamide), poly(vinyl pyrrolidone), poly(ethyleneimine), poly(vinyl imidazole), poly(phosphate), synthetic polypeptides, polyvinyl alkyl ether, polyacryl-and polymethacrylamides, and copolymers of acrylamide and methacrylamide with up to 40% by weight of N-methylene bisacrylamide or N,N-dimethylol urea; polyalkyl aldehydes, water soluble hydrophilic polymers of uncross-linked hydroxyalkyl acrylates and methacrylates, polyalkylene carbonates, and the like. The list is illustrative. Any bioerodible material which is compatible with the drug and non-toxic and which has the desired erosion and release rates can be used.

Without intent to limit the scope of the present invention, the following materials are preferred for use as erodible materials in the intrauterine drug delivery devices:

1. Cross-Linked Gelatin

Gelatin is obtained by the selective hydrolysis of collagen by means well known to those skilled in the art and comprises a complex mixture of water soluble proteins of high molecular weight. As used herein, the term cross-linked gelatin means the reaction product of gelatin or a gelatin derivative with a cross-linking agent reactive with either the hydroxyl, carboxyl or amino functional groups of the gelatin molecule and substantially unreactive with the peptide linkage of the gelatin molecule, the product of reaction having an average molecular weight of from 2,000 to 50,000 between cross-links, although higher values can be employed. Such a product is biodegradable in the environment of the uterus over a prolonged period of time.

Cross-linked gelatin materials are well known to those skilled in the art and can be prepared by reacting the cross-linking agent with gelatin under suitable reaction conditions. The degree to which the gelatin is cross-linked is dependent upon the processing conditions employed to carry out the reaction and markedly affects its characteristics with regard to the time required in order for the material to biodegrade in the eye. The rate and, therefore, the degree of cross-linking of the gelatin is primarily determined by: (1) the effective concentration of reactive groups present; (2) reaction time; (3) temperature at which the reaction is carried out; and (4) pH of the reaction environment. The choice of the particular condition will of course depend on the properties desired for the end product as hereinafter discussed.

Exemplary of suitable cross-linking agents are: aldehydes, such as monoaldehydes, e.g., $C_1$–$C_4$ aldehydes, e.g., acetaldehyde, formaldehyde, acrolein, crotonaldehyde, 2-hydroxy adipaldehyde; dialdehydes, such as glutaraldehyde, glyoxal, other aldehydes such as starch dialdehyde, paraldehyde, furfural and aldehyde bisulfite addition compounds such as formaldehyde bisulfite; aldehyde sugars, e.g., glucose, lactose, maltose, and the like; ketones such as acetone; methylolated compounds such as dimethylol urea, trimethylol melamine; "blocked" methylolated compounds such as tetra(methoxymethyl) urea, melamine; and other reagents such as $C_1$–$C_4$ disubstituted carbodiimides; epoxides such as epichlorohydrin, Eponite 100 (Shell); para-benzene quinone; dicarboxylic acids, e.g., oxalic acid; disulfonic acids, e.g., m-benzene disulfonic acid; ions of polyvalent metals, e.g., chromium, iron, aluminum, zinc, copper; amines such as hexamethylene tetramine; and aqueous peroxydisulfate. See H. L. Needles, *J. Polymer Science*, Part A-1, 5 (1) 1 (1967).

Still another suitable method for cross-linking gelatin is that using irradiation; see for example Y. Tomoda and M. Tsuda, *J. Poly. Sci.*, 54, 321 (1961).

The reactive groups present in gelatin, i.e., hydroxyl, carboxyl and amino functions are present per 100 grams of high quality gelatin in the following approximate amounts: 100, 75 and 50 meq of each of these groups, respectively. The number of reactive sites do not vary appreciably from one gelatin to another, i.e., Type A or B gelatins, unless major hydrolytic breakdown has occurred. These quantities may serve as a general guide in determining the amount of cross-linking agent to be used. However, any discussion of the chemical reactions of gelatin must be made with regard to its very heterogeneous composition. Moreover, actual degradation rates are preferably determined experimentally as hereinafter exemplified in the Examples for a material prepared under a given set of conditions. For example, using formaldehyde as the cross-linking agent, concentrations thereof from 0.01% to 50% by weight, based on the weight of the gelatin in combination with reaction times of 0.1 hours to 5 days and at temperatures of from 4.0° C to 35° C will yield suitable products, the exact combination of concentration, temperature and time depending on the desired dissolution rate. General information on cross-linked gelatin can be found in *Advances in Protein Chemistry*, Vol. VI, Academic Press, 1951, "Cross Linkages in Protein Chemistry," John Bjorksten.

2. Polyesters

Polyesters of the general formula:

I and mixtures thereof, wherein:
  $W$ is a radical of the formula —$CH_2$—; or and;
  $Y$ has a value such that the molecular weight of the polymer is from about 4,000 to 100,000.

These polymers are polymerization condensation products of monobasic hydroxy acids of the formula:

II wherein $n$ has a value of 1 or 2, especially lactic acid and glycolic acid. Also included are copolymers derived from mixtures of these acids. The preparation of polymers of formula I per se, forms no part of the present invention. Several procedures are available and reported by Filachione, et al, *Industrial and Engineering Chemistry*, Vol. 36, No. 3, pp. 223–228, (March 1944; Tsuruta, et al, *Macromol. Chem.*, Vol. 75, pp. 211–214 (1964), and in U.S. Pat. Nos. 2,703,316; 2,668,162; 3,297,033; and 2,676,945.

3. Cross-Linked Anionic Polyelectrolytes

Cross-linked substantially water-insoluble polymeric coordination complexes may be used. A device of these materials can be made by several alternative procedures.

Method A comprises the sequential steps of:
  a. preparing an aqueous solution containing an initially water soluble anionic polyelectrolyte, and adding thereto a polyvalent metal cation capable of coreacting therewith to form a water insoluble cross-linked precipitate;
  b. adding to said mixture drug and a sufficient amount of complexing reagent in the form of an electron donor molecule to render the reaction product water soluble by forming a coordination complex with the reactants;
  c. fabricating the solution into the desired device shape; and then d. substantially removing the electron donor molecule from the system to cross-link the polyelectrolyte and recovering the thus-prepared solid shaped structures.

Alternatively, the complexing reagent and drug can be added to the solution of anionic polyelectrolyte prior to the addition of the polyvalent cation to maintain the reaction product in solution in lieu of resolubilizing the precipitate.

*Method B* comprises the sequential steps of:
a. fabricating a solution of an initially water soluble plasticized anionic polyelectrolyte containing dispersed drug into the desired shape;
b. dipping the thus-formed shape into an aqueous solution of a polyvalent metal cation to crosslink the anionic polyelectrolyte; and
c. recovering the thus prepared water insoluble cross-linked structure.

This material, and the methods for its preparation are the sole invention of Alan S. Michaels. It is more fully described and claimed in his copending application Ser. No. 248,168 owned by the assignee of this invention, filed on Apr. 27, 1972 and now U.S. Pat. No. 3,867,519, and generally described below.

Among the anionic polyelectrolyte polymers which may be interacted to produce the cross-linked structures which are useful in the present invention are those which are soluble in uterine fluids and have a sufficiently high molecular weight, typically at least 10,000, to be solid and capable of forming the required solid body. They contain a plurality of functional groups which are reactive with the polyvalent metal cation to form a salt therewith. Preferably, the functional group is an alkali metal or ammonium salt of a carboxylate, sulfate, sulfonate or phosphate. These functional groups can be characterized as being dissociable anionic groups which are chemically bonded to the polymeric chain. Exemplary of these polymers are: polysaccharides, e.g., K-carrageenin, pectinic acid, heparin sulfate, hyaluronic acid, heparin, natural gums such as algin, locust bean gum, agar, pectin, gum arabic, gum tragacanth; modified natural and synthetic polymers such as carboxymethylcellulose, carboxymethyl starch, polystyrene sulfonic acid, polyvinyl sulfuric acid, poly(vinyl sulfonic acid), polyvinyl methylol sulfonic acid, hydrolyzed poly(vinyl acetate/maleic anhydride), polyvinyl ether-maelic anhydride, poly-(ethylene-maleic anhydride), poly(acrylic acid), poly(-methacrylic acid) and copolymers thereof with acrylic or methacrylic esters, poly(vinyl acetate), poly(vinyl alcohol), poly(vinyl chloride) poly(styrene), and other materials of the same general type.

Preferred embodiments of these materials are the naturally-occurring vegetable-derived water-soluble polysaccharide polymers which are essentially devoid of animal or human toxicity, and which decompose in the body into simple sugars.

The polyvalent metal cations which are interacted with the initially water soluble anionic polyelectrolytes include di, tri or tetra valent metals such as copper, mercury, chromium, nickel, zinc, cobalt, ferric and ferrous iron, aluminum, tin, bismuth, calcium, magnesium, and the like. It is to be understood that any polyvalent metal can be employed which is capable of co-reacting with the polyelectrolyte to form a water-insoluble precipitate and which is innocuous in the body. The anion associated with the metal cation is preferably a halide, e.g., chloride, sulfate or nitrate, although any innocuous ion can be used.

The complexing reagents employed in Method A are any of those materials which are capable of solubilizing or maintaining the polyelectrolyte-polyvalent cationic reaction product in solution so as to enable fabrication of the solution into the desired shape. Exemplary of these materials are primary, secondary and tertiary amines such as mono, di, or trimethyl amine, mono, di or tri-ethanolamine, morpholine, pyridine, piperidine, piperazine, aniline, 2-methyl imidazole, ethylene diamine and higher polyethylene polyamines, and ammonia.

The complexing reagent must be present in solution in an amount sufficient to prevent precipitation of the reactive components. This amount will usually be at least about 0.5% by weight of the total solution, preferably about 5% by weight. Although amounts as great as 50% or more by weight of the total solution may be used, it is unnecessary and frequently undesirable to employ any more than the minimum required to prevent precipitation of the polyelectrolytes. In general, the concentration of the polyelectrolyte must be at least 0.5% by weight and preferably above 1% by weight of the mixture in order to obtain continuous solids in the subsequent processing. Molar ratios of anionic polyelectrolyte to polyvalent metal of from 1 to 10, and preferably from 2 to 5, are satisfactory. The solution thus prepared is then caused to gel by changing conditions so as to permit precipitation to occur by breaking down the coordinate complex so as to cross-link the polymer with metal. Gelation of the polymeric complex solute can be effected by reducing the effective concentration of the complexing reagent by neutralization thereof with acid, or removal in the case of volatile reagents by evaporation in the presence of heated moist air. The required structure can be obtained by the usual process of casting, extruding the mixture, or coating onto a suitable substrate and then drying the formed object by suitable means.

The degree of cross-linking of the polymer by the metal ion can be controlled by adjusting the ratio of metal to polymer in the initial solution, thereby producing materials of varying hydrophilicities. When placed in contact with a uterine fluid, these polymeric structures biodegrade by virtue of the gradual extraction and chelation of the polyvalent ion by endogenous proteins, polysaccharides, and other substances present in this fluid. By varying the degree of cross-linking, the rate of drug release and biodegration can be varied over wide limits. If a natural gum (i.e., algin) is used in the formulation, after dissolution, enzymatic hydrolytic processes will cleave the solubilized polymer into innocuous sugars which are absorbed into the tissues surrounding the uterus.

It is often desired to incorporate plasticizers in the bioerodible materials to improve or vary their physical properties, such as to make them more flexible. Exemplary plasticizers suitable for employment for the present purpose are the pharmaceutically acceptable plasticizers conventionally used, such as acetyl tri-n-butyl citrate, epoxidized soy bean oil, glycerol monoacetate, polyethylene glycol, propylene glycol dilaurate, decanol, dodecanol, 2-ethyl hexanol, 2,2-butoxyethoxyethanol and the like. The proportion of optional plasticizer used will vary within broad limits depending upon the characteristics of the bioerodible material involved. In general, from about 0.01 parts to about 0.2 parts by weight of plasticizer for each part by weight of the bioerodible material can be used.

When plasticizers are included in the bioerodible materials they are most suitably added prior to shaping the final formed structure, such as by dissolving or dispersing them in the solution from which the device is formed.

Drug is released from the delivery devices of this invention by erosion of the polymeric body through which the agent is dispersed. As the body erodes, it releases the dispersed, entrapped drug. The erodible polymer from which the bodies of the device of this invention are formed are substantially imperforate and impermeable to the passage of active agent by diffusion. Hence, the rate of drug release is usually proportional to the rate of material bioerosion. When the rate of bioerosion is constant the rate of release of drug will also be constant, assuming that the dispersion of drug through the body is uniform and that the area of the device which is eroding remains constant.

The aforementioned bioerodible materials erode at a controlled rate when placed in the weakly alkaline aqueous environment of the uterus.

In the devices of this invention, non-erodible materials are often employed as structural elements or core parts. Any polymeric material which is compatible with the tissues and fluids of the uterus may be used including, without limitation, polyolefins, acrylics, non-erodible polyesters and the like. In certain embodiments, it may be of use to employ a swellable hydrophilic polymer in the devices to anchor the devices. Suitable hydrophilic polymers include, for example, polyhydroxyethylmethacrylate and the cross-linked polyacrylamides.

Devices of this invention are useful for delivering all types of drugs to the uterus. In the specification and accompanying claims, the term "drug" broadly includes physiologically or pharmacologically active substances for producing effects in mammals, including humans and primates; avians such as chickens and turkeys; valuable domestic household, sport or farm animals such as horses, dogs, cats, cattle, sheep and the like; or laboratory animals such as mice, monkeys, rats, guinea pigs; and the like.

While the devices of this invention operate with special effectiveness with drugs which have a locallized effect in or upon the uterus, systemically active drugs which act at a point remote from the uterus may be administered as well and are included within the term drugs. Thus, drugs that can be administered by the intrauterine device of the invention include, without limitation: drugs acting on the central nervous system such as, hypnotics and sedatives such as pentobarbital sodium, phenobarbital, secobarbital, thiopental, etc.; heterocyclic hypnotics such as dioxopiperidines, and glutarimides; hypnotics and sedatives such as amides and ureas exemplified by diethylisovaleramide and $\alpha$-bromoisovaleryl urea and the like; hypnotics and sedative alcohols such as carbomal, naphthoxyethanol, methylparaphenol and the like; and hypnotic and sedative urethans, disulfanes and the like; psychic energizers such as isocarboxazid, nialamide, phenelzine, imipramine, tranylcypromine, pargylene and the like; tranquilizers such as chloropromazine, promazine, fluphenazine reserpine, deserpidine, meprobamate, benzodiazepines such as chlordiazepoxide and the like; anticonvulsants such as primidone, diphenylhydantoin, ethotoin, pheneturide, ethosuximide and the like; muscle relaxants and anti-parkinson agents such as mephenesin, methocarbomal, trihexylphenidyl, biperiden, levo-dopa, also known as L-dopa and L-$\beta$-3-4-dihydroxyphenylalanine, and the like; analgesics such as morphine, codeine, meperidine, nalorphine and the like; anti-pyretics and anti-inflammatory agents such as aspirin, salicylamide, sodium salicylamide and the like; local anesthetics such as procaine, lidocaine, naepaine, piperocaine, tetracaine, dibucaine and the like; antispasmodics and anti-ulcer agents such as atropine, scopolamine, methscopolamine oxyphenonium, papaverine; anti-microbials such as penicillin, tetracycline, oxytetracycline, chlorotetracycline, chloramphenicol, sulfonamides and the like; anti-malarials such as 4-aminoquinolines, 8-aminoquinolines and pyrimethamine; hormonal agents such as prednisolone, cortisone, cortisol and triamcinolone; sympathomimetic drugs such as epinephrine, amphetamine, ephedrine, norephineprine and the like; cardiovascular drugs, for example, procainamide, amyl nitrate, nitroglycerin, dipyridamole, sodium nitrate, mannitol nitrate and the like; diuretics, for example, chlorothiazide, flumethiazide and the like; antiparasitic agents such as bephenium hydroxynaphthoate and dichlorophen, dapsone and the like; neoplastic agents such as mechlorethamine, uracil mustard, 5-fluorouracil, 6-thioguanine, procarbazine and the like; hypoglycemic drugs such as insulins, protamine zinc insulin suspension, globin zinc insulin, isophane insulin suspension, and other art known extended insulin suspensions, sulfonylureas such as tolbutamide, acetohexamide, tolazamide, and chlorpropamide, the biguanides and the like; nutritional agents such as vitamins, essential amino acids, essential fats and the like; and other physiologically or pharmacologically active agents.

The devices of this invention deliver with special efficiency progestational substances that have antifertility properties and estrogenic substances that have anti-fertility properties. These substances can be of natural or synthetic origin. They generally possess a cyclopentanophenanthrene nucleus. The term progestational substance as used herein embraces "progestogen" which term is used in the pharmaceutically acceptable steroid art to generically describe steroids possessing progestational activity, and the former also includes "progestins, " a term widely used for synthetic steroids that have progestational effects. The active anti-fertility progestational agents that can be used to produce the desired effects in mammals, including humans, and primates include without limitations: pregn-4-ene-3,20-dione, also known as progesterone; 19-nor-pregn-4-ene-3,20-dione; 17-hydroxy-19-nor-17$\beta$-pregn-5(10)-3n3-20-yn-3-one; dl-11$\beta$-ethyl-17-ethinyl-17-ethinyl-17-$\beta$-hydroxygon-4-ene-3-one; 17$\alpha$-ethinyl-17-hydroxy-5(10)-estren-3-one; 17$\alpha$-ethinyl-19-norestosterone; 6-chloro-17-hydroxypregna-4,6-diene-3, 20-dione; 17$\beta$-hydroxy-6$\alpha$-methyl-17-(1-propynyl)androst-4-ene-3-one; 9$\beta$, 10$\alpha$-pregna-4,6-diene-3,20-dione; 17-hydroxy-17$\alpha$-pregn-4-en-20-yne-3-one; 19-nor-17$\alpha$-pregn-4-3n-20-yen-3$\beta$,17-dial; 17-hydroxy-pregn-4-ene-3,20-dione; 17$\alpha$-hydroxy-progesterone; 17-hydroxy-6$\alpha$-methylpregn-4-ene-3,20-dione; mixtures thereof, and the like.

The estrogenic anti-fertility agents useful herein also include the compounds known as estrogens and the metabolic products thereof that possess anti-fertility properties or that are converted to active anti-fertility agents in the uterine environment. Exemplary estrogenic compounds include β-estradiol, β-estradiol 3-benzoate, 17-β-cyclopentanepropionate estradiol, 1,3,4(10)-estratriene-3,17β-diol dipropionate, estra-1,3,5(10)-triene-3,17-β-diol valerate, estrone, ethinyl estradiol, 17-ethinyl estradiol-3 methyl ether, 17-ethinyl estradiol-3-cyclopentoether, estriol, mixtures thereof, and the like.

Another group of drugs which may be delivered with high efficiency by the devices of this invention include drugs for inducing uterine contractions such as the oxytocic agents, for example, oxytocin, ergot alkaloids such as ergonovine and methylergonomine, quinine, quinidine, histamine and sparteine.

Yet another group of drugs preferred for delivery from the devices of this invention are the prostaglandins. Prostaglandins have a wide range of biological activities.

Prostaglandins occur as natural body humoral agents and are produced synthetically. Such compounds contain an oxygenated cyclopentane nucleus to which two side-chains are attached in the vicinal positions. The hypothetical completely saturated and unsubstituted parent compound of the prostaglandins is called prostanoic acid and is represented by the structural formula:

Nomenclature of the prostaglandins is derived from the above formula and numbering system. Therefore, the structure of the prostaglandin nucleus and side-chains can be described according to the structure of prostanoic acid shown in Formula I.

It has been found that four types of prostaglandin nuclei are present in prostaglandins, which gives rise to four series of prostaglandins commonly designated as E, F, A, and B, which are shown in Formulas II – IV inclusive. In structural formulae II – V, a dotted line represents a valency bond in the α-configuration and the solid line represents a bond in the β-configuration.

Nucleus of Prostaglandins E
II

Nucleus of Prostaglandins F
III

Nucleus of Prostaglandins A
IV

Nucleus of Prostaglandins B
V

Among naturally occurring prostaglandins, two side-chains have been described. One contains a terminal carboxylic acid group and may also contain a double bond, while the other contains a hydroxyl functional group together with one or two double bonds. These side-chains are present in natural prostaglandins in three combinations designated 1,2, and 3, depending upon the total number of double bonds present, so that the natural prostaglandins are designated as $E_1$, $E_2$, $E_3$, $F_1$, $F_2$, etc. These specific side-chains are as follows:

I

| Prostaglandins | $R_1$ | $R_2$ |
|---|---|---|
| $E_1$ $F_1$ $A_1$ $B_1$ | $-(CH_2)_6-COOH$ | $-CH:CHCH(OH)(CH_2)_4CH_3$ |
| $E_2$ $F_2$ $A_2$ $B_2$ | $-CH_2CH:CH(CH_2)_3COOH$ | $-CH:CHCH(OH)(CH_2)_4CH_3$ |
| $E_3$ $F_3$ $A_3$ $B_3$ | $-CH_2CH:CH(CH_2)_3COOH$ | $-CH:CHCH(OH)CH_2CH:CHCH_2CH_3$ |

In addition to the foregoing natural compounds, various biologically active substituted prostaglandins and prostaglandin analogues are known to the art. These include 19-hydroxy prostaglandins, acyl prostaglandins, alkoxy prostaglandins, esters or amides of the carboxyl group in $R_1$, as well as prostaglandins having alkyl substituents on the $R_1$ and $R_2$ side chains.

While any of the natural and synthetic prostaglandins may be delivered by the present devices, those of A, E and F nuclei which have been shown to be most useful for producing uterine contractions comprise a preferred group for use in these devices, a group herein defined to be the uterine-contraction inducing prostaglandins. A more preferred group of prostaglandins comprises those of $E_1$, $E_2$, $F_1$ or $F_2$ configurations, with from 0 to 2 additional alkyl substituents (preferably methyl substituents) on chains $R_1$ and $R_2$. A most preferred group of prostaglandins consists of Prostaglandin $E_1$ (11α, 15(S)-dihydroxy-9-oxo-13-trans-prostenoic acid); Prostaglandin $E_2$ (11α, 15(S)-dihydroxy-9-oxo-5-cis-13-trans-prostadienoic acid); Prostaglandin $F_{2α}$ (9α,11α,15(S)-trihydroxy-5-cis-13-trans-prostatrienoic acid) and the 15-methyl derivative of prostaglandin $F_2^α$. Mixtures of the various prostaglandins, either alone or with added hormonal agents, oxytocin, polypeptides and the like, may be used as well.

The pharmaceutically acceptable, non-toxic salts of the prostaglandins can also be used including the non-toxic alkali metal and alkaline earth metal bases such as sodium, potassium, calcium, lithium, copper, and magnesium hydroxides and carbonates and the ammonium salts and substituted ammonium salts, for example, the non-toxic salts of trialkylamines such as triethylamine, trimethylamine, trisopropylamine, procaine, dibenzylamine, triethanolamine, N-benzyl-beta-phenylethylamine, ethyldimethylamine, benzylamine, N-(lower) alkylpiperidine, N-ethylpiperidine, 2-methylpiperidine and other physiologically acceptable amines and bases.

The above-described prostaglandins are known to the prior art and they are amply described in references such as *Pharmacological Reviews*, Vol. 20, pages 1 to 48, 1968; *Progress In The Chemistry of Fats and Other Lipids*, Vol. IX, pages 231 to 273, 1968; *Science*, Vol. 157, pages 382 to 391; *Angewandte Chemie*, Vol. 4, pages 410 to 416, 1965; *The Journal of Biological Chemistry*, Vol. 238 pages 3555 to 3564, 1963; and other literature references.

The drug is mixed with the bioerodible material and the mixture is fabricated by casting, and the like, into a form suitable for use in the uterus. The erodible material containing drug may be present as the actual intrauterine device or may as well be present as a pendant, flag, or other suitable attachment auxiliary thereto.

The amount of drug present in the device is dependent upon dosage requirements and the length of time the device is to be in place in the uterus and may vary from a single dose of very potent drug, which may be as little as a few micrograms, to an amount sufficient for several hundred or even a thousand doses of a less potent drug, such as up to several grams (for example, 5 grams) of drug. In any event, the amount of drug must be small enough that the erodible material is a continuous phase and the drug is a dispersed phase therein. In general, drug is present in an amount equal to up to about 90% of the weight of bioerodible material. Drug loadings of from about 0.01%, basis bioerodible material, to about 40% are preferred.

The devices of this invention are intended to release drugs locally to the uterus over prolonged periods of time, that is, for periods of from about 3 hours to 30 days or longer. With the progestational and estrogenic substances, delivery times of from about 1 day to 30 days or a year or more are preferred, with dosage rates of from about 10 to 200 mg per day being preferred, thus making it desirable to incorporate at least from about 10 mg to about .6 grams of these substances in a delivery device. When prostaglandins are administered for uterine-contraction inducing purposes, it is preferred to administer the drug over a period of from about 4 hours to about 24 hours at a rate of about 1 microgram/minute to about 25 micrograms/minute. Thus the loading of prostaglandins in the present devices may suitably vary from about 250 micrograms up to as much as about 100 milligrams, depending on the dosage rate and period desired, preferably the loading of prostaglandin would be between about 1 milligram and about 100 milligrams. Similar drug loadings could be determined for the many other drugs suitably delivered by these devices based on their dosage periods and amounts.

The intrauterine devices gradually erode in the uterus and release their drug. The rate of erosion will depend in part on the recipient's temperature (generally from about 35° C to 43° C), uterine pH (generally pH 7-8) and the amount of uterine fluids presently available to contact the device.

The rate of erosion and drug release of materials employed in the invention can be determined experimentally in vitro by testing them under simulated environmental conditions. For example, the rate of erosion of a device in uterine fluids, as would occur with an intrauterine drug delivery device, may be measured by placing a small weighed sample of the material in physiological saline solution - a solution of pH about 7.4 (simulated uterine fluids) at body temperature (37° C), agitating for a timed interval, and periodically measuring the amount of material eroded into the solution. To accurately predict in vivo results, it is necessary to multiply the in vitro rates by an experimentally determined constant which takes into account differences in stirring rate and fluid volumes between the living body and the in vitro test apparatus. This constant may be derived in the cast just set forth by first placing a plurality of small weighed samples of material in a plurality of uteri and sequentially, over a period of time, removing and weighing the samples. The rate thus determined, divided by the rate of erosion observed in vitro with the same material, equals the necessary constant.

For a more complete understanding of the nature of this invention, reference should be made to the following examples which are given merely as further illustrations of the invention and are not to be construed as a limiting sense.

EXAMPLE 1

A bioerodible intrauterine device containing progesterone is prepared in the following manner:

A. Preparation of zinc alginate 1. seven grams of sodium alginate (Keltone, Kelco Co., KT-9529-21) is dissolved in 350 ml of distilled water by means of efficient stirring, to yield a slightly viscous solution.
2. In a separate preparation, 10 grams of zinc chloride is dissolved in 600 ml of distilled water and the pH is adjusted to 3 by drop-wise addition of concentrated hydrochloric acid.
3. To the zinc chloride is added in small proportions the sodium alginate solution under moderate agitation. The mixture is vigorously stirred for 10–15 minutes, and allowed to stand overnight.
4. The precipitate is washed continuously with distilled water to a negative silver chloride test (or to the same conductivity reading as distilled water). The aqueous suspension of the sodium chloride-free zinc alginate is isolated by lyophilization and vacuum-dried at 40° C overnight.

B. Preparation of Progesterone Uterine Insert

1. The mixture containing 1.5 grams of micronized progesterone in 3.5 grams of glycerine is homogenized by means of a suitable colloid mill or by simple grinding of the mixture with mortar and pestle.
2. The resulting white paste is slowly poured into 100 ml of 1.2% ammonium hydroxide solution under vigorous agitation. To this suspension is added 5 grams of zinc alginate previously prepared, and the vigorous agitation is continued until the complete dissolution of the zinc alginate results; if marked thickening occurs, more ammonia solution can be added.
3. The viscous dispersion of (5) is drawn on a glass plate with a wet thickness of ca. 10 mils. The cast plate is placed in a circulating stream of warm, moisturized air at 40° C, and allowed to dry thoroughly.
4. The resulting film is removed from the plate by stripping, and is cut into desired shape and size. For example, a 3 mm × 10 mm device of 3 mil thickness contains about 0.45 mg of progesterone. When inserted in a monkey's uterus, the resulting device releases the drug over a two-day period.

EXAMPLE 2

Cross-linked gelatin devices containing oxytocin are used for the induction of uterine contractions and are prepared as follows:

A phosphate buffer is prepared by addition of one liter of distilled water to 7.1 grams of disodium hydrogen phosphate and 6.9 grams of sodium dihydrogen phosphate monohydrate. The pH is determined to be 6.8. A solution of 0.9 gm glycerin in 40 ml of the phosphate buffer is prepared and 0.15 gm chlorobutanol is added. Upon heating to 90° C and stirring the chlorobutanol is dissolved. Nine grams of gelatin (Atlantic Pharmagel 250 Bloom Type A USP) is added slowly with stirring to the above prepared buffer solution at 90° C. Alternatively, to be more efficient, the gelatin can be added to the vigorously stirred buffer solution after it is cooled to room temperature and then the mixture heated at 90° C until solution is complete.

3.1 grams of oxytocin is added to the stirred gelatin solution as it cools to approximately 50° C. The final mixture is stirred thoroughly for four minutes until the temperature falls to 40° C. It is then poured onto a sheet of polyvinyl chloride which is flattened against a glass plate after moistening the back with water. A film is cast with a doctor's blade adjusted for a wet thickness of 5 mils. The film is allowed to dry by standing at room temperature 1 day.

To cross-link the gelatin a solution of 1% formaldehyde by weight is prepared by addition of 13.1 grams of 38% formaldehyde reagent to 487 grams phosphate buffer (pH 6.8). This volume is sufficient for the treatment of the amount of film prepared as described above. The gelatin films are submerged in this buffered formaldehyde solution for 20 minutes at room temperature, the solution is discarded, and the films are rinsed with water quickly and soaked in ice water for 2 hours. After removal from the ice water and overnight standing at room temperature, the films are prepared for cutting by dipping in water for a few minutes. Excess water is removed and strips are cut from the flexible film and dried at room temperature for several hours. The strips are 25 millimeters in length, 5 millimeters in width and 0.16 millimeter thick. They weigh about 20 mg and contain about 5 mg of oxytocin. The strips are glued to the upper inner surface of plastic cervical rings 2 cm long having outside diameters of 4 cm and inside diameters of 3.5 cm. These rings are inserted in the cervix uteri of first trimester pregnant women. The strips gradually erode releasing oxytocin over a period of about 18 hours thus causing therapeutic abortion. The rings, which additionally serve to dilate the cervix when in place, are then removed.

EXAMPLES 3 and 4

An intrauterine device which releases a prolonged flow of β-estradiol by means of erosion of a body of polymer is fabricated as follows:

First, a mixture of sodium alginate and β-estradiol is formed.

1. A paste containing 0.85 grams of micronized β-estradiol and 5.0 grams of glycerine plasticizer is prepared by grinding the mixture with mortar and pestle.
2. The paste is transferred into a blender containing 0.03 gram Tween 80 (Atlas Chemical Industries), 150 ml distilled water and 7.5 grams of sodium and stirred to complete solution of the alginate.

This liquid mixture is then applied to the bottom 3 cm of conventional Lippes' loops fabricated of 0.2 mm diameter flexible polyethylene rod. This application is by repeated dipping and drying at 40° C. 25 milligrams of dried sodium alginate-plasticizer-β-estradiol are deposited on each loop. The average deposit thickness is about 0.08 mm. Some of the coated loops are immersed in a 5.5% by weight zinc chloride solution (pH 4.5) for 5 hours and some are immersed for 5 hours in a 10% alum ($KAl(SO_4)_2$) solution (pH 3.1) to insolubilize the alginate. The loops are then washed in a 50% glycerine bath until there is no evidence of sodium, potassium, chloride or sulfate ions in the wash.

When the above-coated Lippes' loops are inserted in uteri, they release β-estradiol at a controlled and substantially constant rate. The zinc-containing material erodes over a period of about 6 days, releasing drug at a rate of about 15 micrograms per hour. The aluminum-containing material erodes over about 15 days, releasing drug at a rate of about 5 micrograms per hour. At the completion of therapy, both devices are removed.

EXAMPLES 5 and 6

The preparations of Examples 3 and 4 are repeated with two changes. First, the amount of β-estradiol in the liquid preparation is reduced from 0.85 grams to 0.21 grams. Second, the dipping and drying is continued until 125 milligram deposits are obtained. These devices release drug at ¼ the rates of their Example 3 and 4 counterparts, i.e., at 4 and 1.2 micrograms per hour respectively, but do so for 5 times as long, i.e., 30 days and 75 days respectively.

EXAMPLES 7 – 9

Bioerodible intrauterine devices containing prostaglandins are prepared as follows:

A solution of gelatin (Atlantic Gelatin Pharmagel, A grade) is prepared. To three portions of this solution, each containing the equivalent of 10 grams of dry gelatin, are added respectively: 1.0 grams of the prostaglandin commonly known as $PGF_{2\alpha}$, 0.2 grams of the prostaglandin known as $PGE_2$ and 0.4 grams of $PGE_2$. The drug-gelatin liquid mixtures are then cast on cellulose triacetate surfaces and dried. The materials are then stripped and cut into pieces. Pieces of each of the three materials are placed in 0.05%/w formaldehyde (buffered to pH 7.0) at 25° C for 20 minutes to cross-link the gelatin. The cross-linked product is removed, dried and cut into pieces weighing about 150 milligrams. When these pieces are inserted in a uterus (attached to an intrauterine device) they erode at a constant rate and release respectively:

10 micrograms/minute of $PGF_{2\alpha}$ 2 micrograms/minute of $PGE_2$, and 4 micrograms/minute of $PGE_2$ for all periods of about 24 hours.

These releases of prostaglandins are sufficient to cause uterine contractions and are suitable for effecting therapeutic abortion. Varying the concentration of prostaglandin from about 1% to about 20% basis polymer would give delivery rates of from about 1 $\mu$g/minute to about 20 $\mu$g/minute.

We claim:

1. An intrauterine device for the controlled local administration of drug to the uterus comprising a body formed of a non-toxic bioerodible drug release rate controlling uterine compatible material containing a uterine acceptable drug dispersed therethrough, the device shaped, sized and adapted for insertion and retention in the uterus, and wherein in operation with the device in the environment of use the release rate controlling material is a means which bioerodes to a non-toxic material at a controlled and continuous rate over a prolonged period of time in response to the environment of the uterus, thereby releasing drug to the uterus at a controlled and continuous rate over a prolonged period of time.

2. The device in accordance with claim 1 wherein the drug in the body is a member selected from the group consisting of progestational and estrogenic steroids.

3. The device in accordance with claim 1 wherein the amount of drug in the device is equal up to 90% of the weight of the bioerodible material.

4. The device in accordance with claim 1 wherein the drug in the device is in a pharmaceutical form selected from the group consisting of solid particles, liquid droplets, colloidal particles and gels.

5. The device in accordance with claim 1 wherein the bioerodible material is a member selected from the group consisting of animal and synthetic polymeric materials.

6. The device in accordance with claim 1 wherein the bioerodible material is a plant polymer and the material contains from about 0.01% to about 40% of drug based on the weight of the material.

7. The device in accordance with claim 1 wherein the drug on its release from the device produces a physiological or pharmacological beneficial effect.

8. The device in accordance with claim 1 wherein the body has an outer sleeve formed of a non-toxic, bioerodible drug release rate controlling material containing drug dispersed therein, said sleeve bioeroding over a prolonged period of time in response to the environment of the uterus, thereby releasing drug to the uterus at a controlled rate over a prolonged period of time.

9. The device in accordance with claim 8 wherein the drug in the sleeve is a member selected from the group consisting of progestational and estrogenic steroids possessing antifertility properties.

10. The device in accordance with claim 8 wherein the drug in the sleeve is a member selected from the group consisting of uterine contracting oxytocic and ergot alkaloid drugs.

11. An intrauterine device for the administration of drug to the uterus comprising a core having a configuration shaped, sized and adapted for insertion and placement in the uterus and formed of a non-toxic material that bioerodes in the environment of use to innocuous materials, said core surrounded by a layer formed of a non-toxic bioerodible drug release rate controlling material containing a uterine acceptable drug, and wherein said device when in operation in the environment of use releases drug as the release rate controlling layer bioerodes at a controlled and continuous rate over a prolonged period of time in response to the environment of the uterus, thereby releasing drug at a controlled and continuous rate over a prolonged period of time.

12. The intrauterine device according to claim 11 wherein the core contains up to 6 grams of drug that is released after drug is released from the layer.

13. The intrauterine device according to claim 12 wherein the drug is a member selected from the group consisting of progestational and estrogenic steroids that possess antifertility properties.

14. The intrauterine device according to claim 11 wherein the core and the layer contain more than one drug.

15. The intrauterine device according to claim 11 wherein the core and the layer are formed of different bioerodible materials.

16. The intrauterine device according to claim 11 wherein the drug in the layer is a member selected from the group consisting of progestational and estrogenic steroids having antifertility properties.

17. The intrauterine device according to claim 11 wherein the core and the layer are formed of a separate member selected from the group consisting of naturally occurring and synthetic bioerodible polymeric materials.

18. The intrauterine device according to claim 11 wherein the device contains a member selected from the group consisting of progestational and estrogenic steroids with the device releasing said steroid for a prolonged period of more than a year at rates up to 200 mg per day.

19. The intrauterine device according to claim 11 wherein the configuration comprises a crossbar with a depending leg that is substantially in the shape of a T.

20. An intrauterine device comprising a member formed of a non-erodible, non-toxic material having a structural configuration shaped, sized and adapted for insertion and placement in the uterus, an outer layer on the member formed of a non-toxic bioerodible drug release rate controlling material, a pharmaceutically acceptable drug in the bioerodible layer, and wherein drug is released when the device is placed in the uterus from the release rate controlling material at a controlled and continuous rate as the material bioerodes at a controlled and continuous rate over a prolonged period of time in response to the environment of the uterus.

21. The intrauterine device according to claim 20 wherein the structural member is formed of a flexible, polymeric material that has a uterine-retentive configuration and a memory therefor.

22. The intrauterine device according to claim 20 wherein the member is substantially in the shape of a T.

23. The intrauterine device in accordance with claim 20 wherein the drug in the layer is a member selected from the group consisting of progestational and estrogenic steroids.

24. The intrauterine device in accordance with claim 20 wherein the bioerosion of the layer occurs at a controlled rate when the device is placed in the weakly alkaline environment of the uterus.

25. The intrauterine device in accordance with claim 20 wherein the member contains an uterine acceptable drug that on its release from the device produces a physiological or pharmacological effect.

26. The intrauterine device in accordance with claim 25 wherein the drug is a member selected from the group consisting of progestational and estrogenic steroids.

27. The intrauterine device in accordance with claim 20 wherein the layer defines a sleeve.

28. The intrauterine device according to claim 20 wherein the release rate of drug occurs over a prolonged period of time at a rate of release that is proportional to the rate of bioerosion of the material.

29. The intrauterine device according to claim 20 wherein the layer is formed of a member selected from the group consisting of naturally occurring plant and animal polymeric materials and synthetic bioerodible polymeric materials.

30. An intrauterine device comprising a member formed of a non-erodible, non-toxic material having a structural configuration shaped, sized and adapted for insertion and placement in a uterus, the device having an outer layer on the member formed of a drug release rate controlling bioerodible material comprising a polyester of the general formula:

$$-[-O-(W)-CO-]_y-$$

wherein: $W$ is a radical of the formula $-CH_2-$ or and $y$ has a value such that the molecular weight of the polymer is from about 4,000 to 100,000, said layer containing a pharmaceutically acceptable drug that is released when the device is placed in the uterus as the material bioerodes at a controlled and continuous rate over a prolonged period of time.

31. The method according to claim 30 wherein the core contains antifertility drug that is released in an effective amount into the uterus for interfering with the reproductive process.

32. An intrauterine device comprising a member formed of a non-erodible, non-toxic material having a structural configuration shaped, sized and adapted for insertion and placement in a uterus, the device having an outer layer on the member formed of cross-linked gelatin containing steroid dispersed therein, and wherein the device when in the environment of use releases steroid as the layer bioerodes at a controlled and continuous rate over a prolonged period of time.

33. An intrauterine device comprising a member formed of a non-erodible, non-toxic material having structural configuration shaped, sized and adapted for insertion and placement in the uterus, an outer layer on the member containing a steroid and formed of a cross-linked gelatin that is prepared by cross-linking gelatin with an agent selected from the group consisting of aldehydes and ketones at a concentration of 0.01% to 60% by weight, based on the weight of gelatin, and a temperature of from 4.0° C to 35° C for a reaction period of from 0.1 hour to 5 days, and wherein the steroid is released at a controlled and continuous rate when the device is placed in the uterus from the release rate controlling material as the material bioerodes at a controlled and continuous rate over a prolonged period of time in response to the environment of the uterus.

34. An intrauterine device comprising a member formed of a non-erodible, non-toxic material having a structural configuration shaped, sized and adapted for insertion and placement in the uterus, an outer layer on the member formed of a material selected from the group of bioerodible drug release rate controlling materials consisting of collagen, algin, pectin, carrageenin, chitin, chondroitin sulfate, agar-agar, guar, gum arabic, tragacanth, starch, oxystarch, starch succinate, starch esters, hydroxylated cotton, poly(vinyl alcohol), poly(lactic acid), poly(glycolic acid), poly(ethylene oxide), poly(acrylamide), poly(vinyl pyrrolidone), poly(electrolytes), poly(vinyl imidazole), poly(peptides), poly(methacrylamide), and copolymer of acrylamide and methacrylamide, a pharmaceutically acceptable drug in the layer, and wherein drug is released at a controlled and continuous rate when the device is placed in the uterus from the material as the material bioerodes at a controlled and continuous rate over a prolonged period of time.

35. An intrauterine device comprising a member formed of a non-erodible, non-toxic poly(olefin) having a structural configuration shaped, sized and adapted for insertion and placement in the uterus, an outer layer on the member formed of a bioerodible drug release rate controlling material, a pharmaceutically acceptable drug in the material, and wherein drug is released at a controlled and continuous rate when the device is placed in the uterus from the material as the material bioerodes at a controlled and continuous rate over a prolonged period of time.

36. A method for interfering with the reproductive physiology of a female animal including humans by locally administering an effective amount of an antifertility drug within the uterus of the animal, said method comprising: inserting into the uterus and positioning therein an intrauterine device formed of a non-toxic bioerodible drug release rate controlling material containing antifertility drug dispersed therethrough, the device shaped, sized and adapted for insertion and placement in the uterus, and, wherein drug is released into the uterus at a controlled and continuous rate over a prolonged period of time as the release rate material bioerodes to a non-toxic material at a controlled and continuous rate over a prolonged period of time in response to the environment of the uterus with the rate of release of drug proportional to the rate of bioerosion over the prolonged period of time.

37. A method for interfering with the reproductive physiology of a female animal including humans by administering an effective amount of an antifertility drug within the uterus of the animal, said method comprising: inserting into the uterus and positioning therein a device comprising a core having a configuration shaped, sized and adapted for insertion and placement in the uterus and formed of a non-toxic material that bioerodes in the environment of use to an innocuous material, a layer formed of a non-toxic bioerodible drug release rate controlling material surrounding the core, a uterine acceptable antifertility drug present in the layer, and, wherein drug is released into the uterus at a controlled and continuous rate over a prolonged period of time as the release rate layer bioerodes at a controlled and continuous rate over a prolonged period of time in response to the environment of the uterus with the rate of release of drug proportional to the rate of bioerosion of the layer over the prolonged period of time.

38. A method for interfering with the reproductive physiology of a female animal including humans by administering an effective amount of an antifertility drug within the uterus of the animal, said method comprising: inserting into the uterus a device comprising a member formed of a non-erodible, non-toxic material having a structural configuration shaped and size adapted for insertion and placement in the uterus, an outer layer on the member formed of a non-toxic drug release rate controlling bioerodible material, a drug in the layer that is released when the device is placed in the uterus, and, releasing the drug into the uterus at a controlled and continuous rate over a prolonged period of time as the release rate layer bioerodes in response to the environment of the uterus over a prolonged period of time.

39. A method according to claim 38 wherein the member is a polymeric material and contains a uterine acceptable drug.

40. A method according to claim 38 wherein the rate of release of drug corresponds to the rate of bioerosion.

41. A method according to claim 38 wherein the layer contains a pharmaceutically acceptable drug selected from the group consisting of progestational and estrogenic steroids.

42. A method for interfering with the reproductive process of a female animal including humans, said method comprising the steps of inserting into the uterus a device comprising a crossbar and a depending leg and formed of a non-erodible material, an outer layer on the device formed of a non-toxic drug release rate controlling bioerodible material, a drug in the layer that is released when the device is placed in the uterus, and, releasing the drug into the uterus at a controlled and continuous rate over a prolonged period of time as the release rate layer bioerodes in response to the environment of the uterus over a prolonged period of time.

43. A method for interfering with the reproductive process according to claim 42 wherein the device is substantially in the shape of a T.

44. A method for interfering with the reproductive process according to claim 42 wherein the layer contains a drug selected from the group consisting of naturally occurring and synthetic steroids.

45. A method for interfering with the reproductive process according to claim 42 wherein the layer is formed of a member selected from the group consisting of plant, animal and synthetic polymeric materials.

46. A method for interfering with the reproductive process according to claim 42 wherein the layer is formed of a bioerodible member selected from the group consisting of collagen, cross-linked gelatin, algin, pectin, carrageenin, chitin, chondroitin sulfate, agar-agar, guar, gum arabic, starch, oxystarch, carboxymethyl starch, aminoethyl starch, starch maleate, starch succinate, starch benzoate, starch acetate, poly(vinyl alcohol), poly(lactic acid), poly(acrylamide), poly(vinyl pyrrolidone), poly(glycolic acid), poly(vinyl imidazole), poly(peptides), poly(methacrylamide), copolymers of acrylamide and methacrylamide, and water soluble polymers of uncross-linked hydroxyalkyl acrylates and methacrylates.

47. A method for interfering with the reproductive process according to claim 42 wherein the drug in the layer is a member selected from the group consisting of progestational and estrogenic steriods.

* * * * *